United States Patent
Refsell

(10) Patent No.: US 9,750,259 B2
(45) Date of Patent: Sep. 5, 2017

(54) PYROXASULFONE AND GLUTAMINE SYNTHESIS INHIBITOR COMPOSITIONS FOR WEED CONTROL

(71) Applicant: Valent U.S.A., Walnut Creek, CA (US)

(72) Inventor: Dawn Refsell, Lathrop, MO (US)

(73) Assignee: Valent U.S.A., Corporation, Walnut Creek, CA (US)

(*) Notice: Subject to any disclaimer, the term of this patent is extended or adjusted under 35 U.S.C. 154(b) by 0 days.

(21) Appl. No.: 14/946,995

(22) Filed: Nov. 20, 2015

(65) Prior Publication Data

US 2016/0143287 A1    May 26, 2016

Related U.S. Application Data

(60) Provisional application No. 62/083,512, filed on Nov. 24, 2014.

(51) Int. Cl.
*A01N 43/80* (2006.01)
*A01N 57/20* (2006.01)
*A01N 43/38* (2006.01)

(52) U.S. Cl.
CPC ............. *A01N 57/20* (2013.01); *A01N 43/80* (2013.01)

(58) Field of Classification Search
None
See application file for complete search history.

(56) References Cited

U.S. PATENT DOCUMENTS

2010/0190794 A1  7/2010  Hupe et al.
2011/0065579 A1  3/2011  Sievernich et al.

OTHER PUBLICATIONS

International Search Report and Written Opinion issued by the International Bureau as PCT/US15/61784 on Feb. 5, 2016.
Bruce et al., "Horseweed (*Conyza canadensis*) control in no-tillage soybeans (*Glycine max*) with preplant and preemergence herbicides", Weed Technology, 1990, vol. 4, pp. 642-647.

*Primary Examiner* — John Pak
*Assistant Examiner* — Daniel Branson
(74) *Attorney, Agent, or Firm* — Wood, Phillips, Katz, Clark & Mortimer

(57) ABSTRACT

The present invention is directed to compositions containing herbicidal mixtures of pyroxasulfone and glutamine synthesis inhibitors. The present invention is further directed to methods of increasing the activity of a glutamine synthesis inhibitor with the compositions of the present invention.

11 Claims, No Drawings

PYROXASULFONE AND GLUTAMINE SYNTHESIS INHIBITOR COMPOSITIONS FOR WEED CONTROL

FIELD OF THE INVENTION

The present invention relates to agricultural compositions useful for controlling weeds, and methods of use thereof.

BACKGROUND OF THE INVENTION

Unwanted plants, such as weeds, reduce the amount of resources available to crop plants and can have a negative effect on crop plant yield. Commonly unwanted plants in crop plant environments include broadleaf plants and grasses.

Herbicides are used to kill unwanted plants, such as weeds, in crop plant environments. Herbicides are expensive, and their use may result in unintentional consequences such as groundwater contamination, environmental damage, herbicide-resistant weeds, and human and mammalian health concerns. It is therefore desirable to minimize the amount of herbicides applied to a crop-growing environment or any area in need of weed control.

Unwanted plants, such as weeds, may greatly reduce yields of crop plants. For example, a Horseweed infestation reportedly was responsible for an 80% reduction in soybean yields. Bruce, J. A., and J. J. Kells, *Horseweed (Conyza Canadensis) control in no-tillage soybeans (Glycine max) with preplant and preemergence herbcides*, Weed Technol. 4:642-647 (1990). Therefore, controlling weeds, and especially grasses and Horseweed, is a major concern of crop growers.

Further, Horseweed and other grasses are becoming resistant to the widely used herbicide glyphosate. As early as 2000, glyphosate resistant Horseweed was reported in Delaware. Glyphosate resistant Horseweed has since been reported in numerous states. Accordingly, there is a need for new products that can provide effective kill rates of glyphosate resistant Horseweed.

Weeds are also becoming resistant to herbicides that inhibit acetolactate synthase (ALS) and protoporphyrinogen oxidase (PPO). Horseweed has also been reported to be resistant to 2,4-D and dicamba. Accordingly, there is a need for new technology to control weeds that are resistant to commercially available herbicides.

In most fields throughout the Midwest and Mid-South, in-crop burndown applications are the only options for controlling Horseweed due to weather and timeliness of applications. Repeated applications of these chemistries have contributed to expanding resistance and lack of control. Repeated applications of single effective active ingredients will only continue to select for resistant populations of weeds, thus leaving no alternatives for weed control other than mechanical. Mechanical removal of weeds requires extensive use of resources and is not an option for no-till or highly erodible land.

No-till farming has been increasing in popularity because it has many benefits, including decreased labor time and decreased soil erosion. However, one of the downsides of no-till farming is that weeds are harder to control in these areas because they are not subjected to tilling. Accordingly, there is an increasing need for alternative ways to handle weed infestation.

Pyroxasulfone (3-[[[5-(difluoromethoxy)-1-methyl-3 (trifluoromethyl)-1H-pyrazol-4-yl]methyl]sulfonyl]-4,5-dihydro-5,5-dimethylisoxazole) is an herbicide that has residual weed control. Pyroxasulfone, however, does not have post emergence weed control. Pyroxasulfone is commercially available in a mixture with flumioxazin (Fierce®, available from Valent U.S.A. Corporation).

Glufosinate (DL-4-[hydroxy](methyl)phosphinoyl]-DL-homoalaninate) and its salts such as DL-glufosinate-ammonium are known to have herbicidal activity and are commercially available, e.g. Basta™ and Liberty™ (available from Bayer CropSciences). Glufosinate is a phosphinic acid that inhibits the activity of glutamine synthetase which results in ammonium accumulation in the plants. The ammonia destroys the cells which inhibits photosynthesis. Bialaphos is another glutamine synthesis inhibitor that is naturally produced by a soil microorganism.

When applied alone, glufosinate often yields unsatisfactory weed control. Several applications and/or high dosage rates are required for high efficacy. Further, glufosinate has little effect of some broadleaf species and rhizomatous grasses. In an effort to overcome these shortcomings, glufosinate is frequently applied with at least one additional herbicide, such as 2,4-D, dicamba, triazines such as atrazine or metribuzin, chloroacetanilides such as metholachloror dimethenamid (including dimethenamid-P), linuron and/or pendimethalin. However, the effectiveness of such combinations is often not satisfactory and high application rates are still required to achieve acceptable control of grass weeds and broadleaves. Moreover, the reliability of such combinations depends strongly on the weathering conditions and certain difficult to control weed species may escape. In addition, the herbicidal activity of these compositions persists only for a short time, which allows effective burndown only within a small timeframe prior to planting a crop. Moreover, the persistence of the herbicidal activity strongly depends upon the weathering conditions.

U.S. Patent Application Publication No. 2011/0065579 discloses thousands of mixtures of herbicides, one of which is a mixture of glufosinate and pyroxasulfone in a ratio range of from 2000:1 to 1:10. However, this publication fails to provide guidance within this broad range of acceptable amounts of glufosinate or pyroxasulfone. Further, this publication does not teach or suggest narrower ratios that would produce acceptable results. In addition, this publication fails to suggest the synergy that Applicants discovered between glutamine synthesis inhibitors and pyroxasulfone.

In summary, there is a need for a composition that reduces the amount of herbicides necessary to obtain sufficient weed control while minimizing the harm to crop plants. As more weeds become resistant to herbicides, alternative compositions with high weed control are desired. Further, as no-till farming continues to increase in popularity, there is a greater need for effective herbicides. A composition with effective weed control and lower dosage rate will lead to increased crop plant yields, and decreased environmental, human, and mammalian health concerns.

SUMMARY OF THE INVENTION

In one aspect, the present invention is directed to agricultural compositions comprising pyroxasulfone and a glutamine synthesis inhibitor, or an agriculturally acceptable salt thereof, in a ratio of from about 1:0.5 to about 1:20.

In another aspect, the present invention is directed to methods for increasing the activity of a glutamine synthesis inhibitor comprising applying the agricultural compositions of the present invention to an area in need of weed control.

DETAILED DESCRIPTION OF THE INVENTION

It was surprisingly discovered that pyroxasulfone can significantly increase the burndown activity of glutamine synthesis inhibitors when applied to weeds by as much as 3-fold compared to a glutamine synthesis inhibitor applied alone. This finding was unexpected because pyroxasulfone applied by itself has no post emergent control.

Compositions of the present invention containing a mixture of pyroxasulfone and at least one glutamine synthesis inhibitor, or an agriculturally acceptable salt thereof, will provide the end user with consistent herbicidal activity. The compositions will also provide residual weed and grass control.

In one embodiment, the present invention is directed to agricultural compositions comprising pyroxasulfone and a glutamine synthesis inhibitor, or an agriculturally acceptable salt thereof, in a ratio of from about 1:0.5 to about 1:20. In a preferred embodiment, the compositions contain from about 1:1 to about 1:10 of pyroxasulfone:glutamine synthesis inhibitor, or an agriculturally acceptable salt thereof. In a more preferred embodiment, the compositions contain from about 1:3 to about 1:8 of pyroxasulfone:glutamine synthesis inhibitor, or an agriculturally acceptable salt thereof. In an even more preferred embodiment, the compositions contain from about 1:4 to about 1:7 of pyroxasulfone:glutamine synthesis inhibitor, or an agriculturally acceptable salt thereof. In a most preferred embodiment, the compositions contain from about 1:5 to about 1:6.6 of pyroxasulfone:glutamine synthesis inhibitor, or an agriculturally acceptable salt thereof.

The glutamine synthesis inhibitor of the present invention can be selected from any herbicide that is classified by the Herbicide Resistance Action Committee ("HRAC") as group H or the Weed Science Society of America ("WSSA") as group 14. In another embodiment, the glutamine synthesis inhibitor in compositions of the present invention is glufosinate, an agriculturally acceptable salt thereof, or bialaphos. In a preferred embodiment, the glutamine synthesis inhibitor is glufosinate. In a more preferred embodiment, the glutamine synthesis inhibitor is the ammonium salt of glufosinate.

In yet another embodiment, the compositions of the present invention also contain an herbicide classified by HRAC as group E or the WWSA as group 14 (inhibitors of protoporphyrinogen oxidase). In a preferred embodiment, this herbicide is flumiclorac or flumiclorac-pentyl. Flumiclorac (2-[2-chloro-4-fluoro-5-(1,3,4,5,6,7-hexahydro-1,3-dioxo-2H-isoindol-2-yl)phenoxy]acetic acid) is a dicarboximide herbicide that has preemergence activity.

In an embodiment, the present invention is directed to methods for increasing the activity of a glutamine synthesis inhibitor comprising applying an agricultural composition comprising pyroxasulfone and a glutamine synthesis inhibitor, or an agriculturally acceptable salt thereof, in a ratio of about 0.05 to about 1:20, or from about 1:1 to about 1:10 to an area in need of weed control. In a preferred embodiment, the compositions that are applied to the area in need of weed control contain from about 1:3 to about 1:8 of pyroxasulfone:glutamine synthesis inhibitor, or an agriculturally acceptable salt thereof. In a more preferred embodiment, the compositions that are applied to the area in need of weed control contain from about 1:4 to about 1:7 of pyroxasulfone:glutamine synthesis inhibitor, or an agriculturally acceptable salt thereof. In a most preferred embodiment, the compositions that are applied to the area in need of weed control contain from about 1:5 to about 1:6.6 of pyroxasulfone:glutamine synthesis inhibitor, or an agriculturally acceptable salt thereof.

In an embodiment, from about 50 to about 150 grams per hectare of pyroxasulfone is applied to the area in need of weed control. In a preferred embodiment, from about 70 to about 110 grams per hectare of pyroxasulfone is applied to the area in need of weed control. In a more preferred embodiment, from about 80 to about 100 grams per hectare of pyroxasulfone is applied to the area in need of weed control. In a most preferred embodiment, about 90 grams per hectare of pyroxasulfone is applied to the area in need of weed control.

In an embodiment, from about 100 to about 1,000 grams per hectare of glutamine synthesis inhibitor is applied to the area in need of weed control. In a preferred embodiment, from about 300 to about 700 grams per hectare of glutamine synthesis inhibitor is applied to the area in need of weed control. In a more preferred embodiment, from about 400 to about 650 grams per hectare of glutamine synthesis inhibitor is applied to the area in need of weed control. In a most preferred embodiment, from about 450 to about 600 grams per hectare of glutamine synthesis inhibitor is applied to the area in need of weed control.

In an embodiment, from about 100 to about 1,000 grams per hectare of glufosinate, or an agriculturally acceptable salt thereof, is applied to the area in need of weed control. In a preferred embodiment, from about 300 to about 700 grams per hectare of glufosinate, or an agriculturally acceptable salt thereof, is applied to the area in need of weed control. In a more preferred embodiment, from about 400 to about 650 grams per hectare of glufosinate, or an agriculturally acceptable salt thereof, is applied to the area in need of weed control. In a most preferred embodiment, from about 450 to about 600 grams per hectare of glufosinate, or an agriculturally acceptable salt thereof, is applied to the area in need of weed control.

In another embodiment of the invention, flumiclorac-pentyl is also applied to the area in need of weed control. In an embodiment, from about 14 to about 116 grams per hectare of flumiclorac-pentyl is applied to the area in need of weed control. In a preferred embodiment, from about 14 to about 90 grams per hectare of flumiclorac-pentyl is applied to the area in need of weed control. In a most preferred embodiment, from about 14.5 to about 73 grams per hectare of flumiclorac-pentyl is applied to the area in need of weed control.

In a further embodiment, the weed controlled by the compositions of the present invention is at least one of Horseweed (*Conyza Canadensis*), Large Crabgrass (*Digitaria sanguinalis*), Palmer Amaranth (*Amaranthus palmeri*), Broadleaf Signalgrass (*Brachiaria platyhylla*), Common Barnyardgrass (*Echinochloa crus-galli*), Yellow Nutsedge (*Cyperus esculentus*), Eclipta (*Eclipta prostrate*), Lamb's quarters (*Chenopodium*), Velvetleaf (*Abutilon theophrasti*), and Giant Foxtail (*Setaria faberi*). In a preferred embodiment, the weed controlled is Palmer Amaranth. In another preferred embodiment, the weed controlled is Horseweed.

In an embodiment of the invention, the pyroxasulfone and glutamine synthesis inhibitor, or an agriculturally acceptable salt thereof, are applied concurrently to the area in need of weed control. In another embodiment, the pyroxasulfone and glutamine synthesis inhibitor, or an agriculturally acceptable salt thereof, are applied sequentially to the area in need of weed control.

In a preferred embodiment, the glutamine synthesis inhibitor of the present invention is glufosinate. In another preferred embodiment, the glutamine synthesis inhibitor of the present invention is the ammonium salt of glufosinate.

Applicants' mixtures can be applied by any convenient means. Those skilled in the art are familiar with the modes of application that include foliar applications such as spraying, chemigation (a process of applying the mixture through the irrigation system), by granular application, or by impregnating the mixture on fertilizer.

Applicants' mixtures can be prepared as concentrate formulations or as ready-to-use formulations. The mixtures can be tank mixed.

The herbicide mixtures of the present invention may be formulated to contain adjuvants, such as solvents, anticaking agents, stabilizers, defoamers, slip agents, humectants, dispersants, wetting agents, thickening agents, emulsifiers, and preservatives which increase the long lasting activity of the actives. Other components that enhance the biological activity of these ingredients may optionally be included.

Methylated seed oil ("MSO") is an adjuvant that improves leaf cuticle penetration of an agricultural active, such as a plant growth regulator, fungicide or herbicide. MSO can be used in the mixtures of the present invention, but is not required or responsible for the synergy of the combination the herbicides of the present invention. Other oil based adjuvants with similar qualities could also be used, such as crop oil concentrates.

Mixtures of the present invention can be formulated to contain a liquid solvent. Examples of solvents include water or oil concentrates.

Applicants' mixtures can also include one or more additional herbicides.

The mixtures of the present invention can be applied to any environment in need of weed control. The environment in need of weed control may include any area that is desired to have a reduced number of weeds or to be free of weeds. For example, the herbicide combination can be applied to an area used to grow crop plants, such as a field, orchard, or vineyard. For example, Applicants' compositions and methods can be applied to areas where soybeans, corn, peanuts, and cotton are growing. In a preferred embodiment, the mixture is applied in an area where a broadleaf crop (soybean, cotton, peanut, orchard, vineyard, forages) is growing. The mixtures of the present invention can also be applied to non-agricultural areas in need of weed control such as a lawns, golf courses, or parks.

Applicants' compositions and methods can be applied successfully to crop plants and weeds that are resistant to glyphosate, glufosinate, or other herbicides. The composition and methods can also be applied to areas where genetically modified crops ("GMOs") or non-GMO crops are growing. The term "GMO crops" as used herein refers to crops that are genetically modified.

When used in this application, Horseweed refers to *Conyza Canadensis*, Large Crabgrass refers to *Digitaria sanguinalis*, Palmer Amaranth refers to *Amaranthus palmeri*, Broadleaf Signalgrass refers to *Brachiaria platyhylla*, Common Barnyardgrass refers to *Echinochloa crus-galli*, Yellow Nutsedge refers to *Cyperus esculentus, Eclipta* refers to *Eclipta prostrata*. Although the composition of the present invention has proven synergy when applied to Horseweed and Palmer amaranth, the synergistic composition could be applied to any number of other weeds or undesired plants for effective control and is not limited to the examples. These could include Giant Ragweed (*Ambrosia trifida*), Common Ragweed (*Ambrosia artemisiifolia*), and Velvetleaf (*Abutilon theophrasti*).

Throughout the application, the singular forms "a," "an," and "the" include plural reference unless the context clearly dictates otherwise.

As used herein, all numerical values relating to amounts, weight percentages and the like are defined as "about" or "approximately" each particular value, plus or minus 10%. For example, the phrase "at least 5.0% by weight" is to be understood as "at least 4.5% to 5.5% by weight." Therefore, amounts within 10% of the claimed values are encompassed by the scope of the claims.

As used herein, "post emergence" refers to an herbicide treatment that is applied to an area after the weeds have germinated and emerged from the ground or growing medium.

As used herein, "burndown" refers to when an herbicide is used to reduce weed presence at the time of treatment. Burndown is often used in minimum or no-till fields because the weeds cannot be managed by tilling the soil. The burndown application may be used post-harvest and/or prior to crop emergence. Burndown is especially useful against weeds that emerge between growing seasons.

As used herein, synergy means that when combined, the claimed composition achieves a result that is greater than the expected result.

These representative embodiments are in no way limiting and are described solely to illustrate some aspects of the invention.

Further, the following example is offered by way of illustration only and not by way of limitation.

EXAMPLE

Example 1

The following field test was conducted. Roundup Ready soybeans (*Glycine max*) were used in the test as the crop plant. All of the treatments contained MSO concentrate oil at 1% v/v.

When the test began, the test plot had weeds that were less than 24 inches tall. Treatments were administered at the concentrations as follows. Glufosinate-ammonium was administered at 593 grams/hectare. Pyroxasulfone was administered at 90 grams/hectare throughout the experiment.

On 14 DAT, readings were taken to determine the survival of Palmer Amaranth. On 21 DAT, readings were taken to determine the residual control of Palmer Amaranth and Horseweed. Survival ratings were taken by counting the number of alive and dead plants at the time of the reading. All data was analyzed using Bartlett's test and with p value of 0.5 for determining significance of the results. The results of this study can be seen below in "Table 1. The Effect of Glufosinate and Pyroxasulfone on Weeds."

TABLE 1

The Effect of Glufosinate and Pyroxasulfone on Weeds

| | Herbicide | Rate (grams of active per hectare) | Palmer amaranth (<2" tall) | Residual control of Palmer amaranth | Horseweed (bolted) |
|---|---|---|---|---|---|
| 1 | glufosinate | 593 | 90 | 93 | 75 |
| 2 | pyroxasulfone | 90 | 5 | 99 | 0 |
| 3 | glufosinate pyroxasulfone | 593 90 | 99 | 99 | 97 |
| 4 | glufosinate | 593 | 99 | 99 | 99 |

TABLE 1-continued

The Effect of Glufosinate and Pyroxasulfone on Weeds

| Herbicide | Rate (grams of active per hectare) | Palmer amaranth (<2" tall) | Residual control of Palmer amaranth | Horseweed (bolted) |
|---|---|---|---|---|
| pyroxasulfone | 90 | | | |
| flumiclorac-pentyl | 73 | | | |

The results illustrate that a composition of glufosinate and pyroxasulfone is synergistic. Pyroxasulfone alone provides only 5% control of Palmer Amaranth, however, when combined with glufosinate, the combination provided a 99% kill rate. Glufosinate alone could only achieve a 90% kill rate. For Horseweed, pyroxasulfone provides no (zero percent) residual control of Horseweed. In contrast, the combination of pyroxasulfone and glufosinate provided a 97% kill rate.

What is claimed is:

1. An agricultural composition for controlling Palmer Amaranth and Horseweed comprising pyroxasulfone and glufosinate, or an agriculturally acceptable salt thereof, in a ratio of about 1:6.6.

2. The composition of claim 1 further comprising flumiclorac-pentyl.

3. A method of increasing the activity of glufosinate comprising applying an agricultural composition comprising pyroxasulfone and glufosinate in a ratio of about 1:6.6 to an area in need of Horseweed or Palmer Amaranth control.

4. The method of claim 3 wherein the pyroxasulfone is applied at a rate of from about 50 to about 150 grams per hectare.

5. The method of claim 3 wherein the pyroxasulfone is applied at a rate of from about 70 to about 110 grams per hectare.

6. The method of claim 3 wherein the pyroxasulfone is applied at a rate of from about 80 to about 100 grams per hectare.

7. The method of claim 3 wherein glufosinate is applied at a rate of from about 100 to about 1000 grams per hectare.

8. The method of claim 3 wherein glufosinate is applied at a rate of from about 300 to about 700 grams per hectare.

9. The method of claim 3 wherein glufosinate is applied at a rate of from about 450 to about 600 grams per hectare.

10. The method of claim 3 further comprising applying flumiclorac-pentyl to the area in need of Horseweed or Palmer Amaranth control.

11. The method of claim 3 wherein the pyroxasulfone and glufosinate, or agriculturally acceptable salt thereof, are applied concurrently or sequentially to the area in need of Horseweed or Palmer Amaranth control.

* * * * *

Adverse Decision in Interference

Patent No. 9,750,259, Dawn Refsell, PYROXASULFONE AND GLUTAMINE SYNTHESIS INHIBITOR COMPOSITIONS FOR WEED CONTROL, Interference 106,124, final judgment adverse to the patentee rendered December 2, 2020, as to claims 1-11.

*(Official Gazette February 8, 2022)*